United States Patent
Baandrup et al.

(10) Patent No.: US 11,554,261 B2
(45) Date of Patent: Jan. 17, 2023

(54) SYSTEM FOR ELECTRICAL STIMULATION DURING FUNCTIONAL MRI

(71) Applicants: Roskilde/Køge Hospital, Roskilde (DK); Rigshospitalet, Copenhagen (DK); University Of Copenhagen, Copenhagen K (DK)

(72) Inventors: Anders Ohlhues Baandrup, Frederiksberg C. (DK); Louise Møller Jørgensen, Gentofte (DK); Carsten Thomsen, Lyngby (DK)

(73) Assignees: Roskilde/Køge Hospital, Roskilde (DK); Rigshospitalet, Copenhagen (DK); University Of Copenhagen, Copenhagen (DK)

( * ) Notice: Subject to any disclaimer, the term of this patent is extended or adjusted under 35 U.S.C. 154(b) by 0 days.

(21) Appl. No.: 16/650,713

(22) PCT Filed: Oct. 5, 2018

(86) PCT No.: PCT/EP2018/077166
§ 371 (c)(1),
(2) Date: Mar. 25, 2020

(87) PCT Pub. No.: WO2019/068884
PCT Pub. Date: Apr. 11, 2019

(65) Prior Publication Data
US 2020/0282209 A1    Sep. 10, 2020

(30) Foreign Application Priority Data

Oct. 6, 2017   (EP) .................................... 17195244

(51) Int. Cl.
*A61N 1/08* (2006.01)
*A61N 1/36* (2006.01)
(Continued)

(52) U.S. Cl.
CPC ........... *A61N 1/086* (2017.08); *A61N 1/0456* (2013.01); *A61N 1/0534* (2013.01);
(Continued)

(58) Field of Classification Search
CPC .. A61N 1/086; A61N 1/36062; A61N 1/0456; A61N 1/0534; A61N 1/0551;
(Continued)

(56) References Cited

U.S. PATENT DOCUMENTS 7,076,292 B2    7/2006  Forsberg
8,644,943 B2    2/2014  Choe et al.
(Continued)

FOREIGN PATENT DOCUMENTS

DE     10355652 A1     6/2005
EP     3113838 A1 *   1/2017  ......... A61N 1/36014
(Continued)

OTHER PUBLICATIONS

Arantes et al Performing functional magnetic resonance imaging in patients with Parkinson's disease treated with deep brain stimulation. Mov Disord. Aug. 2006;21(8):1154-62. doi: 10.1002/mds.20912. PMID: 16671094 (Year: 2006).*

(Continued)

*Primary Examiner* — Niketa Patel
*Assistant Examiner* — Michael A Rizzuto
(74) *Attorney, Agent, or Firm* — Hamilton, Brook, Smith & Reynolds, P.C.

(57) ABSTRACT

The present disclosure relates to a system for generating a predefined electrical signal in an MR scanner for use in electrical stimulation of a subject during MRI or functional MRI of said subject, wherein said MR scanner is located inside a shielded MRI room. The system comprises a control unit to be located outside the MRI room for generating an electrical signal and an electrical to optical converter to be (Continued)

located outside the MRI room for converting said electrical signal to a corresponding optical signal. An optical transmitting element, such as an optical fiber, is used for transmitting the optical signal into the MRI room, and an optical to electrical converter is used for converting the optical signal to said predefined electrical signal for electrical stimulation of the subject during magnetic resonance imaging. The optical to electrical converter is configured for being located inside the MRI room and for operation during magnetic resonance imaging.

16 Claims, 2 Drawing Sheets

(51) Int. Cl.
  *A61N 1/04*    (2006.01)
  *A61N 1/05*    (2006.01)
  *H04B 1/58*    (2006.01)

(52) U.S. Cl.
  CPC ....... *A61N 1/0551* (2013.01); *A61N 1/36007* (2013.01); *A61N 1/36062* (2017.08); *H04B 1/587* (2013.01)

(58) Field of Classification Search
  CPC .. A61N 1/36007; A61N 1/08; A61N 1/37211; A61N 1/37217; H04B 1/587
  See application file for complete search history.

(56) References Cited

U.S. PATENT DOCUMENTS

| | | |
|---|---|---|
| 2007/0434040 | 2/2007 | Deimling |
| 2011/0093032 A1* | 4/2011 | Boggs, II ............. A61N 1/3611 607/42 |
| 2012/0109260 A1* | 5/2012 | Stancer ............. A61N 1/39622 607/60 |
| 2014/0275970 A1 | 9/2014 | Brown et al. |
| 2016/0228005 A1* | 8/2016 | Bammer ............. A61B 5/0059 |
| 2016/0239627 A1* | 8/2016 | Cerny .................. G06F 3/0486 |

FOREIGN PATENT DOCUMENTS

| | | |
|---|---|---|
| EP | 3113838 B1 | 1/2017 |
| JP | 2014-000116 A | 1/2014 |
| JP | 2014-017809 A | 1/2014 |
| KR | 10-1308896 B1 | 9/2013 |

OTHER PUBLICATIONS

International Search Report and Written Opinion of the International Searching Authority dated Jan. 18, 2019 in PCT/EP2018/077166 "System for Electrical Stimulation During Functional MRI" (18 pages).

Notification Of Transmittal Of The International Preliminary Report on Patentability dated Jan. 15, 2020 in PCT/ EP2018/077166 "System for Electrical Stimulation During Functional MRI" (19 pages).

Paula R. Arantes et al: "Performing functional magnetic resonance imaging in patients with Parkinson's disease treated with deep brain stimulation", Movement Disorders, vol. 21, No. 8, Jan. 1, 2006 (Jan. 1, 2006), pp. 1154-1162, XP055654222, US ISSN: 0885-3185, DOI: 10.1002/mds.20912 (9 pages).

* cited by examiner

SYSTEM FOR ELECTRICAL STIMULATION DURING FUNCTIONAL MRI

This application is the U.S. National Stage of International Application No. PCT/EP2018/077166, filed Oct. 5, 2018, which designates the U.S., published in English, and claims priority under 35 U.S.C. § 119 or 365(c) to European Application No. 17195244.3, filed Oct. 6, 2017. The entire teachings of the above applications are incorporated herein by reference.

The present invention relates to a system for generating a predefined electrical signal in an MR scanner for use in electrical stimulation of a subject during functional magnetic resonance imaging.

BACKGROUND OF INVENTION

Electrical stimulation is a well-recognized treatment method used primarily in cardiac and neurolopsychiatric: Cardiac arrhythmia, Parkinson's Disease, essential tremor, Tourette's Syndrome, epilepsy, but also for obsessive compulsive disorders, headache and pain. Electrical stimulation can for example be applied in the form of a cardiac pacemaker, Deep Brain Stimulation (DBS), Spinal Cord Stimulation (SCS), Vagus Nerve Stimulation (VNS) or Transcutaneous Nerve Stimulation (TENS). The clinical effect of electrical stimulation is well-established in cardiac diseases and neurological movement disorders such as Parkinson, essential tremor and Tourette's syndrome, but DBS is also a promising treatment in neuropsychiatric disorders such as depression and anxiety, addiction and obesity cognitive enhancement and dementia, headaches and migraines, obsessive compulsive disorders as well as in bionics, rehabilitation therapy, pain therapy, otologic disorders, gastro-intestinal disorders, urogenital disorders, ophthalmological disorders, autoimmune and rheumatological disorders, inflammatory-related disorders, and voice therapy.

Functional magnetic resonance imaging (fMRI) is a measurement technique that measures brain activity by detecting changes associated with blood flow. Cerebral blood flow and neuronal activation are coupled, and the fMRI is thereby able to map the brain activity. Likewise, fMRI can be conducted in other parts of the body of interest, e.g., the spinal cord or the heart. Combining electrical stimulation with fMRI may be useful e.g. for imaging the physiological response of the electrical stimulation applied to the subject. For the purpose of treating neuropsychiatric disorders it is also very beneficial to detect brain activity while simultaneously adjusting the stimulation parameters. However, delivering a stimulation signal to a subject during fMRI is problematic. During fMRI the subject is exposed to very strong magnetic fields and powerful radio frequency (RF), which may interfere with electronics and alter the programmed settings of a stimulation unit. Additionally, electrical devices used to deliver an electrical stimulus may induce large artifacts and disruption of the obtained MR image. A MRI room, where the MRI or fMRI is recorded, is shielded like a Faraday cage to avoid electrical fields to enter the MRI room and to reduce the leakage of strong magnetic fields and RF waves out of the MRI room. Locating the stimulation device outside the MRI room and connecting the stimulation unit to the subject using cables may also be problematic due to interference and possible RF heating of the cable. Therefore, a means is sought for delivering an adjustable electrical impulse to a subject with an implanted electrode while the subject is placed in an MR scanner without disrupting or altering the delivered electrical signal or interfering with the MRI.

A system for MRI compatible communications has been developed at the Mayo Clinic in Rochester, USA, wherein wireless communication modules are used to communicate between inside and outside the MRI room. The system is disclosed in patent application US2014275970.

SUMMARY OF INVENTION

In a first aspect the present disclosure relates to a system for generating a predefined electrical signal in an MR scanner for use in electrical stimulation of a subject during MRI or functional MRI of said subject, wherein said MR scanner is located inside a shielded MRI room. The system comprises a control unit to be located outside the MRI room for generating an electrical signal and an electrical to optical converter to be located outside the MRI room for converting said electrical signal to a corresponding optical signal. An optical transmitting element, such as an optical fiber, is used for transmitting the optical signal into the MRI room, and an optical to electrical converter is used for converting the optical signal to said predefined electrical signal for electrical stimulation of the subject during magnetic resonance imaging. The electrical stimulation can be transferred to the subject by one or more needles or electrodes placed on (e.g. surface electrode for transcutaneous nerve stimulation (TENS)), implanted into (requires surgical procedure, where e.g. the brain is exposed, used for DBS and for VNS) or inserted into (e.g. a needle for electromyography, subcutaneous stimulation, pacemakers the subject. For DBS, e.g., one or more electrodes can be used that is implanted in the brain. For other types of stimulations other types of needles or electrodes will be suitable to be placed on, implanted in or inserted of the subject.

The optical to electrical converter is configured for being located inside the MRI room and for operation during magnetic resonance imaging. The optical to electrical converter can be a solar cell. The optical signal from the optical transmitting element is illuminated onto the solar cell. An electrical signal corresponding to the optical signal can be generated by the solar cell using e.g. the photovoltaic effect or the photoelectric effect. The solar cell can be a photodiode. Using the photoelectric effect or the photovoltaic effect in e.g. a photodiode will be a simple and cost-effective solution.

An electronic circuit can be placed in one or both of the conductors connecting the optical to electrical converter like a solar cell to the electrode or needle. The electronic circuit can process the incoming signal before the signal is transferred to the electrode/needle. The transformation can be lowering the effective voltage or potential so that the effective voltage is useable for the specific treatment. The skilled person will know if and how the electronic circuit has to and can transform the incoming signal before the signal is transferred to the electrode. The necessary transformation will depend on the electrode and the application for which the electrode/needle is used. With the standard electrode or needle used in DBS, SCS, TENS, peripheral nerve stimulation (PNS), cranial nerve stimulation, VNS, electrical muscle stimulation, cortical multi-electrode stimulation, retinal multi-electrode stimulation, gastric electrical stimulation therapy or cardiac stimulation, as well as surface electrical stimulation, non-invasive electrical stimulation, transcorneal electrical stimulation (TES), whole-eye electrical stimulation (WES), transcutaneous electrical nerve stimulation (TENS), subcutaneous nerve stimulation, neuromuscular electrical stimulation (NMES), bionic replacements/bionic implants/neuroprosthetics, cochlear implants, electroceuticals/electrobionics or similar stimulations. As an example, the resistance of brain tissue is not less than 700Ω, and an applied voltage of around 3 or 3.5 V in this situation will be suitable. With the electrode(s) placed on, inserted into, or implanted into another tissue the resistance may be different and a suitable applied voltage may also have another value than the applied voltage for brain tissue.

To ensure that the right and especially not too high signal or potential is applied on the electrode, the electronic circuit can have a feedback system, where the applied signal or potential on the electrode is used as an input for the electronic circuit to lower the output potential of the electronic circuit if the applied signal is too high and vice versa. The feedback system may have to be tuned or set for the type of tissue, where the electrode(s) is placed, inserted, or implanted.

The electronic circuit can be made of only passive components, i.e. components that consume but do not produce energy and/or components that are incapable of power gain. That will be a very-cost-effective electronic circuit.

The circuit comprising the solar cell like a photo diode, the conductors, the electronic circuit, and the needle or electrode can preferably be made disposable. Such a circuit will be time effective, since no re-sterilization is necessary, and cost-effective, since the circuit can be produced at low costs.

The end of the optical transmitting element or the optical fiber can have an optical diffuser for spreading the optical signal onto the solar cell, preferably onto the whole solar cell. That will increase the efficiency of the optical to electrical conversion process.

For clinical settings with electric stimulation therapy, especially, safety is of vital importance. The presently disclosed invention makes it possible to conduct fMRI of patients while simultaneously performing electrical stimulation to an implanted electrode in a safe and controllable manner. The magnetic field in an MR scanner can possibly destroy or alter the programmed settings in an electrical stimulation unit, which thereby can deliver an uncontrolled and potentially dangerous electrical stimulation to an electrode implanted in or placed on the subject. Locating the control unit outside the MRI room means that it is not exposed to the strong magnetic field from the scanner, thereby eliminating the risk of the signal being altered therefrom. This also means that personnel in the control room outside the scanner can fully control the delivered signal during fMRI.

By using a fiber optic cable to communicate between the control unit outside the MRI room and the equipment delivering the stimulation to the subject inside the MRI room, no electrically conducting cables are used, meaning that the cable will not interfere with other cables or the MR scanner and no RF heating of the cable will occur. Additionally, there is no signal delay between control unit and delivery to the subject when using a fiber optic cable for communicating the signal, whereas a wireless connection may involve some signal delay. Using a fiber optic cable also provides a solid connection where the risk of signal interruption is low. The electrical devices used to deliver an electrical stimulus may induce large artefacts and disruption of the obtained MR image caused by interference with the MRI signal. When locating this equipment outside the shielded MRI room, the interference from such equipment is eliminated.

The electric signal can be generated in a processor or a computer that controls an optical signal generator that generates a corresponding optical signal. The optical signal generator will function as an electrical to optical converter, since an electric signal corresponding to the output optical signal of the optical signal generator is present in the processor or the computer. The processor or the computer will function as the control unit generating the electrical signal.

A second aspect of the invention relates to a system for electrical stimulation of a subject during MRI or functional MRI of said subject. The system comprises the system for generating a predefined electrical signal according to the first aspect of the invention, and at least one electrode configured for being implanted in the subject and configured for delivering the electrical stimulation to the subject based on said predefined electrical signal. In one embodiment the at least one electrode contains a plurality of contacts for delivering the electrical stimulation to the subject. The system may also be configured for delivering the electrical stimulation to the subject through multiple electrodes.

A third aspect of the invention relates to a method for generating a predefined electrical stimulation signal for electrical stimulation of a subject during MRI or functional MRI wherein said subject is located in an MR scanner located inside a shielded MRI room. The method comprises the steps of 1) generating an electrical signal outside the MRI room, 2) converting the electrical signal to an optical signal outside the MRI room, 3) transmitting the optical signal into the MRI room, and 4) converting the optical signal to said predefined electrical stimulation signal inside the MRI room.

The present disclosure further relates to a method for electrical stimulation of a subject during MRI or functional MRI of said subject in an MR scanner located inside a shielded MRI room. The method comprises the steps of; converting an electrical stimulation signal to an optical signal outside the MRI room, transmitting the optical signal inside the MRI room using a fiber optic cable, converting the optical signal back to the electrical stimulation signal inside the MRI room, and subjecting the subject to the electrical stimulation signal.

The present disclosure further relates to disposable kit of a solar cell electrically connected to at least one electrode for use in stimulating a subject during MRI or functional MRI wherein said subject is located in an MR scanner located inside a shielded MRI room.

The optical signal from the optical transmitting element or the optical fiber is illuminated onto the solar cell that will generate an electric potential. That is transferred to the electrode. The solar cell, the electrode, and the electrical connection between them form a kit that is so simple and cost-effective that the manufacturing costs are lower than the re-sterilization process of the kit. If the solar cell is a photodiode the manufacturing costs will be even lower. The electrical connection can be wires or the solar cell is mounted directly on the electrode. To simplify the disposal and recycling process, the solar cell and the electrode can easily be disconnected from each other so that the solar cell can be recycled as electrical parts and the electrode as metal.

The disposable kit can further comprise an electronic circuit positioned in one or both of the conductors connecting the optical to electrical converter like a solar cell to the electrode or needle. The electronic circuit of the disposable kit can have all the characteristics and advantages of the electronic circuit as described above.

The circuit comprising the solar cell like a photo diode, the conductors, the electronic circuit, and the needle or electrode can preferably be made disposable. Such a circuit will be time effective, since no re-sterilization is necessary, and cost-effective, since the circuit can be produced at low costs.

DETAILED DESCRIPTION OF THE INVENTION

Figure 1:
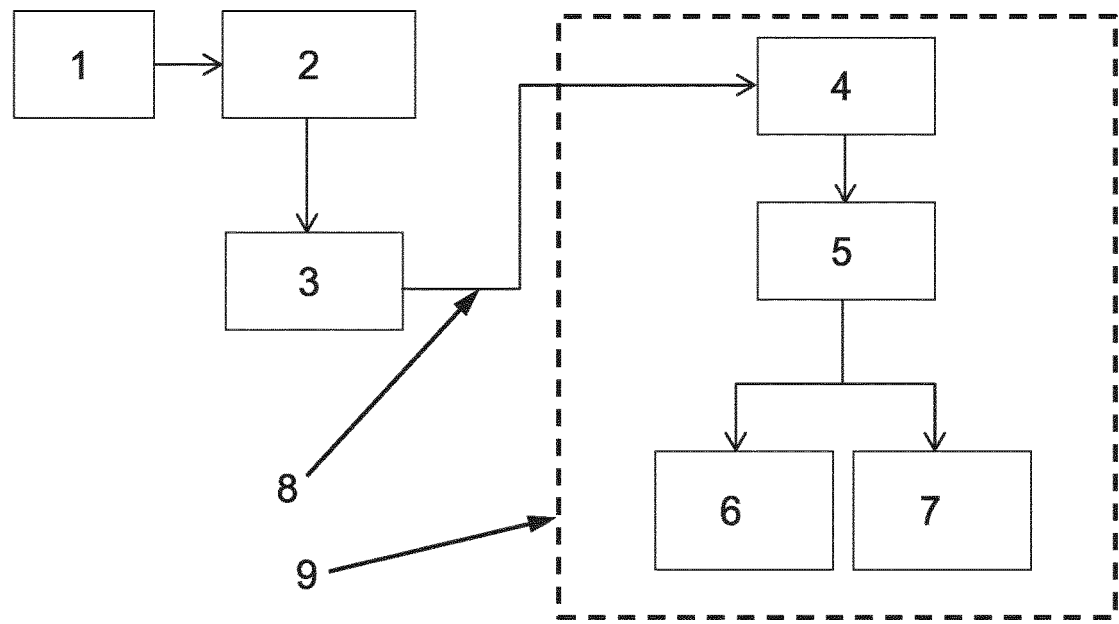
FIG. 1 is a diagram showing one embodiment of the presently disclosed invention. The figure shows the MRI room with a trigger box from the fMRI equipment, a signal generator and an electrical to optical converter located outside the MRI room. An optical to electrical converter, a voltage converter and electrodes are located inside the MRI room.

The first aspect of the invention relates to a system for generating a predefined electrical signal in an MR scanner for use in electrical stimulation of a subject during MRI or fMRI of said subject. Here, stimulation during MRI or fMRI also covers stimulation before a MR scan is initiated and stimulation between MRI sequences. The system and method may be used for any type of electrical stimulation of a subject. In one embodiment of the invention the electrical stimulation of the subject is selected from the group of: deep brain stimulation, spinal cord stimulation, transcutaneous nerve stimulation, peripheral nerve stimulation, cranial nerve stimulation, vagal nerve stimulation, electrical muscle stimulation, cortical multi-electrode stimulation, retinal multi-electrode stimulation, gastric electrical stimulation therapy and cardiac stimulation, as well as surface electrical stimulation, non-invasive electrical stimulation, transcorneal electrical stimulation (TES), whole-eye electrical stimulation (WES), transcutaneous electrical nerve stimulation (TENS), subcutaneous nerve stimulation, neuromuscular electrical stimulation (NMES), bionic replacements/bionic implants/neuroprosthetics, cochlear implants, and electroceuticals/electrobionics.

The present invention involves converting an electrical signal to an optical signal for transmitting the signal into an MRI room. In one embodiment the electrical to optical converter uses a transistor for converting the signal. The transistor may be used to power e.g. a light emitting diode or a laser which is then coupled to the fiber optic cable for transmitting the signal into the MRI room. The electrical signal being converted could be any type of signal, e.g. a TTL signal.

The optical signal generated by the converter is sent through an optical transmitting element, such as a fiber optic cable, into the MRI room. The optical transmitting element may also comprise a free-space optical communication system. In one embodiment the fiber optic cable comprises at least one single-mode fiber for transmitting the optical signal. In some embodiments the system comprises more than one fiber optic cable for communicating a signal into the MRI room. Such a design may be used for sending the same signal through different fiber optic cables for redundancy. Different fiber optic cables may also be used for sending separate stimulation signals through different cables, which may be useful for stimulation through different contacts on the same electrode or for stimulation through different electrodes.

Inside the MRI room the optical signal received from the at least one fiber optic cable is converted back to an electrical signal. In one embodiment the optical to electrical converter uses a phototransistor or an optocoupler for converting the signal. The signal may be converted back to the original signal used to create the optical signal, e.g. a TTL signal, or to another signal corresponding to the electrical stimulation signal. The electrical signal from the optical to electrical converter may therefore not be exactly the same as the electrical signal generated by the signal generator. For example, the voltage of the electrical signal from the optical to electrical converter could be different from the voltage of the signal from the signal generator. The voltage of the stimulation signal may also be adjusted by a voltage converter before exposing the subject to the signal. As stated previously the optical to electrical converter may merely be at least one solar cell which provides for a simple and cost effective solution, because the solar cell can be driven by the energy from the light in the optical signal.

The electrical stimulation signal from the optical to electrical converter inside the MRI room is used for stimulating the subject. In one embodiment of the invention the system further comprises at least one electrode configured for being implanted in the subject and configured for delivering the electrical stimulation to the subject based on said predefined electrical signal. In another embodiment the at least one electrode contains a plurality of contacts for delivering the electrical stimulation to the subject. Specifically, the Medtronic DBS 3389 electrode with four contacts may be used in some embodiments. In yet another embodiment more than one electrode is used for multi-electrode stimulation of the subject.

The optical to electrical converter is preferably powered by a battery. Powering the equipment inside the MRI room using a battery may be advantageous because there are fewer wires, which makes it simpler to connect to the equipment, and this configuration could reduce interference with the signal from the MR scanner. Usually there is access to mains electricity inside an MR scanner. The power for the equipment inside the MRI room may therefore alternatively be provided by mains electricity.

The electrical stimulation signal for stimulating the subject may be customized according to the subject, the medical condition of the subject and the type of treatment for the subject. In one embodiment the parameters defining the electrical signal for the electrical stimulation of the subject include one or more of the stimulation voltage, stimulation current, impedance of the system, stimulation frequency, stimulation duty cycle, total duration of the stimulation signal and the waveform of the stimulation signal. The waveform of the signal may be adjusted for optimizing the treatment of the subject. In one embodiment at least part of the electrical signal for the electrical stimulation of the subject is periodic with a rectangular waveform, or a square waveform, or a triangle waveform, or a sinusoidal waveform, or a cosine waveform, or a sawtooth waveform, or a ramp waveform, or an exponential waveform. In another embodiment the electrical signal changes between two or more of the mentioned waveforms. The signal type may also be adjusted or changed for the stimulation of the subject. Therefore, in another embodiment the electrical signal for the electrical stimulation of the subject is pulsating or alternating or switching between pulsating and alternating.

For electrical stimulation of a subject several parameters may need to be adjusted for optimizing the treatment of the subject. In one embodiment of the invention the voltage of the electrical stimulation signal is in the range 0.1-10 V, or in the range 0.5-8.0 V, or in the range 1.0-6.0 V, or in the range 1.5-5.0 V, or in the range 2.0-4.0 V, or in the range 2.5-3.5 V. In another embodiment of the invention the voltage of the electrical stimulation signal is up to 120 V used e.g. in muscle stimulation. In another embodiment the frequency of the electrical stimulation signal is in the range 0-240 Hz, or in the range 20-240 Hz, or in the range 60-200 Hz, or in the range 80-180 Hz, or in the range 100-160 Hz, or in the range 120-140 Hz. The electrical stimulation signal may in some embodiments be comprised of multiple frequencies. In yet another embodiment the duty cycle of the electrical stimulation signal is less than 0.4, or less than 0.25, or less than 0.15, or less than 0.1, or less than 0.05, or less than 0.03. The signal may also be characterized in terms of the width of each pulse in the signal. This pulse width may in some embodiments be in the range 10-500 microseconds, or in the range 30-350 microseconds, or in the range 50-250 microseconds, or in the range 70-180 microseconds, or in the range 80-120 microseconds. The impedance of the system influences the current flowing in the electrical stimulation signal. An excessive current may be dangerous to the subject treated with the stimulation. Therefore, in another embodiment the impedance of the system is in the range 1100-1400 Ohm, or in the range 800-1700 Ohm, or in the range 600-1900 Ohm, or in the range 300-2200 Ohm.

The stimulation signal for stimulating the subject may be on continuously, such that the subject is stimulated throughout the treatment, or it may be turned on and off at different times during the treatment. The electrical stimulation signal may also be varied during the treatment. In one embodiment at least one of the stimulation voltage, stimulation current, impedance of the system, stimulation frequency and stimulation duty cycle is varied during the electrical stimulation of the subject. As mentioned earlier, different stimulations signals may also be used for stimulation of the subject through different contacts on an electrode or using different electrodes. In another embodiment the stimulation therefore consists of multiple different signals for stimulation through different contacts or electrodes.

For electrical stimulation treatment of a subject, it is preferred that the signal delivered to the subject is the indeed the signal sent from a control unit and that no alteration of the signal occurs. This may be monitored by using the electrical stimulation signal from the optical to electrical converter in the MRI room to generate an electrical verification signal. The verification may then be converted to an optical signal and transmitted through a fiber optical cable outside the MRI room where it may be converted to an electrical signal and used for verifying that the correct stimulation signal is used for treating the subject. Therefore, in one embodiment the system is configured for, during magnetic resonance imaging: 1) monitoring the electrical stimulation signal delivered to the subject to generate an electrical verification signal, 2) converting said electrical verification signal to an optical verification signal, 3) transmitting said optical verification signal out of the MRI room, and 4) converting said optical verification signal to an electrical signal for monitoring the stimulation delivered to the subject in real time. The optical verification signal may be transmitted out of the MRI room using a separate fiber optic cable or using the fiber optic cable used for transmitting the optical stimulation signal into the MRI room. The system may furthermore be configured for stopping the electrical stimulation of the subject if the verification signal deviates from the stimulation signal, thereby providing added safety for the treatment.

The stimulation parameters and other adjustments for the stimulation are preferably controlled from a computer. Therefore, in one embodiment the system further comprises a computer configured for receiving input parameters for the electrical stimulation and configured for controlling the equipment. The medical staff thereby has full control over the signal generated and can change and adjust the signal according to the requirements of the treatment. In another embodiment the system further comprises a signal generator, such as an oscilloscope, configured for generating the electrical stimulation signal. The oscilloscope is preferably configured for receiving a signal from the computer, said signal defining the electrical stimulation signal.

The third aspect of the invention relates to a method for generating a predefined electrical stimulation signal for electrical stimulation of a subject during MRI or functional MRI of said subject. In this method, the optical signal may be transmitted into the MRI room using a fiber optic cable or a free-space communication system. In one embodiment the predefined electrical stimulation signal is suitable for: deep brain stimulation, spinal cord stimulation, transcutaneous nerve stimulation, peripheral nerve stimulation, cranial nerve stimulation, vagus nerve stimulation, electrical muscle stimulation, cortical multi-electrode stimulation, retinal multi-electrode stimulation, gastric electrical stimulation therapy or cardiac stimulation, as well as surface electrical stimulation, non-invasive electrical stimulation, transcorneal electrical stimulation (TES), whole-eye electrical stimulation (WES), transcutaneous electrical nerve stimulation (TENS), subcutaneous nerve stimulation, neuromuscular electrical stimulation (NMES), bionic replacements/bionic implants/neuroprosthetics, cochlear implants, and electroceuticals/electrobionics. In another embodiment the method further comprises the steps of 1) generating an electrical verification signal inside the MRI room from the predefined electrical stimulation signal, 2) converting said electrical verification signal to an optical verification signal, 3) transmitting said optical verification signal out of the MRI room, and 4) converting said optical verification signal to an electrical signal for monitoring the stimulation delivered to the subject in real time. The optical verification signal may be transmitted out of the MRI room using a fiber optic cable or a free-space communication system.

The present disclosure further relates to a method for electrical stimulation of a subject during fMRI in an MR scanner located inside a shielded MRI room. In one embodiment of the invention the type of treatment for which the method is used is selected from the group of: deep brain stimulation, spinal cord stimulation, transcutaneous nerve stimulation, peripheral nerve stimulation, cranial nerve stimulation, vagus nerve stimulation, electrical muscle stimulation, cortical multi-electrode stimulation, retinal multi-electrode stimulation, gastric electrical stimulation therapy and cardiac stimulation, as well as surface electrical stimulation, non-invasive electrical stimulation, transcorneal electrical stimulation (TES), whole-eye electrical stimulation (WES), transcutaneous electrical nerve stimulation (TENS), subcutaneous nerve stimulation, neuromuscular electrical stimulation (NMES), bionic replacements/bionic implants/neuroprosthetics, cochlear implants, and electroceuticals/electrobionics. In another embodiment the method further comprises the step of converting the electrical stimulation signal delivered to the patient inside the MRI room to an optical signal and transmitting said optical signal outside the MRI room through a fiber optic cable. One purpose of this step is to create a verification signal from the electrical stimulation signal sent to the subject such that the delivered stimulation signal can be monitored outside the MRI room. The equipment is preferably operated and controlled using a computer. Therefore, in yet another embodiment the method further comprises the step of inputting stimulation parameters to a computer configured for generating commands for the electrical stimulation.

DETAILED DESCRIPTION OF THE DRAWINGS

FIG. 1 is a diagram of one embodiment of the invention. This embodiment shows the MRI room 9 with a trigger box 1 from the fMRI equipment, a signal generator 2 and an electrical to optical converter 3 located outside the MRI room. The trigger box 1 is configured for sending a trigger signal to the signal generator 2 when the fMRI scan is initiated. The signal generator 2 generates the predefined electrical signal for the electrical stimulation of the subject according to predefined stimulation parameters. The electrical stimulation signal is sent to an electrical to optical converter 3 which generates a corresponding optical signal. The optical signal is then transmitted through a fiber optic cable 8 into the MRI room 9. Inside the MRI room 9 an optical to electrical converter 4 converts the optical signal received from the fiber optic cable 8 back to an electrical signal which is sent to a voltage converter 5 that converts the voltage of the signal to e.g. 3 V. The electrical stimulation signal is sent to at least one electrode (in the example in the figure the signal is sent to two electrodes 6, 7) which is implanted in the subject, thereby stimulating the subject with the predefined electrical signal.

Figure 2:
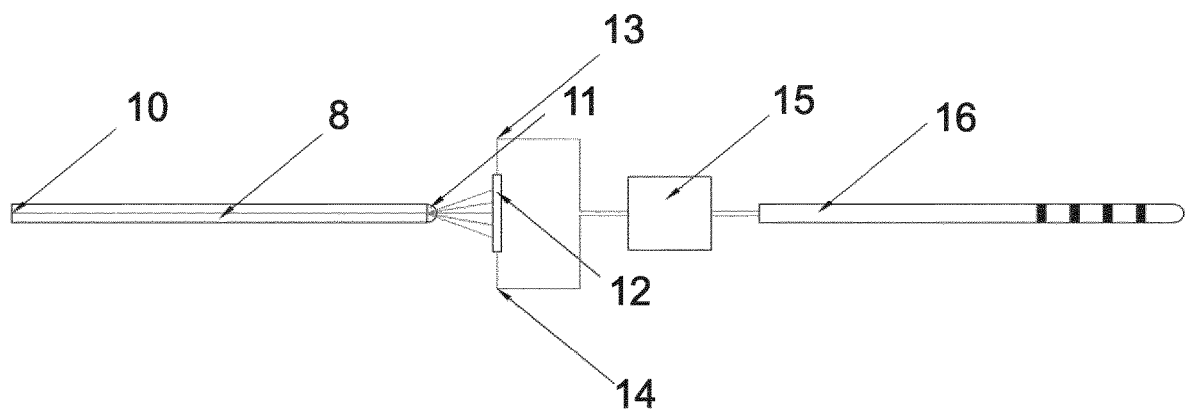
FIG. 2 is a schematic drawing of one example how the optical signal inside the MRI room is transferred into a corresponding electrical signal.

FIG. 2 shows the setup inside the MRI room, where an optical signal 10 travelling in the fiber optic cable 8, enters from outside the MRI room into the MRI room. At the end of the fiber optic cable 8, an optical diffuser 11 spreads the optical signal 10 onto a solar cell 12. The voltage or current in the solar cell can e.g. be generated by the photovoltaic effect or by the photoelectric effect. The solar cell can be a photodiode.

The solar cell generates a voltage signal corresponding to the optical signal 10, where the voltage signal is over the two conductors 13, 14. The conductors 14 can be connected to ground. The voltage signal enters an electronic circuit 15, which may process the incoming voltage signal before the signal is transferred to, e.g., a deep brain stimulation electrode 16 such as a Medtronic DBS needle 3389 (Medtronic; Dublin, Ireland), used for deep brain stimulation.

This setup has been shown to yield a sufficiently high output in an experiment, where two high efficiency solar cells (SLMD960H09L, IXYS, Milpitas, Calif., US) in serial were used. The two solar cells were illuminated with one high density LED (LZP-00CW0R, LED Engin, San Jose, Calif., US). The LED was mounted at the end of a 2.5 m long liquid light guide (3 mm MK Liquid, Olympus, Tokyo, Japan) and at the other end of the liquid light guide the solar cell was placed. The solar cell was short-circuited with 700 ohms, which is the minimum impedance in the human brain. At this test setup, more than 40 mW could be achieved. The voltage level was 5.3V with 700 ohms.

The electronic circuit 15 can comprise an electronic circuit for protecting the patient for hazardous high voltages. In other applications than deep brain stimulation other electrodes/needles can be used. The skilled person will know if and how the electronic circuit 15 has to process the incoming signal before the signal is transferred to the electrode. The necessary processing will depend on the electrode and the application for which the electrode is used.

Figure 3:
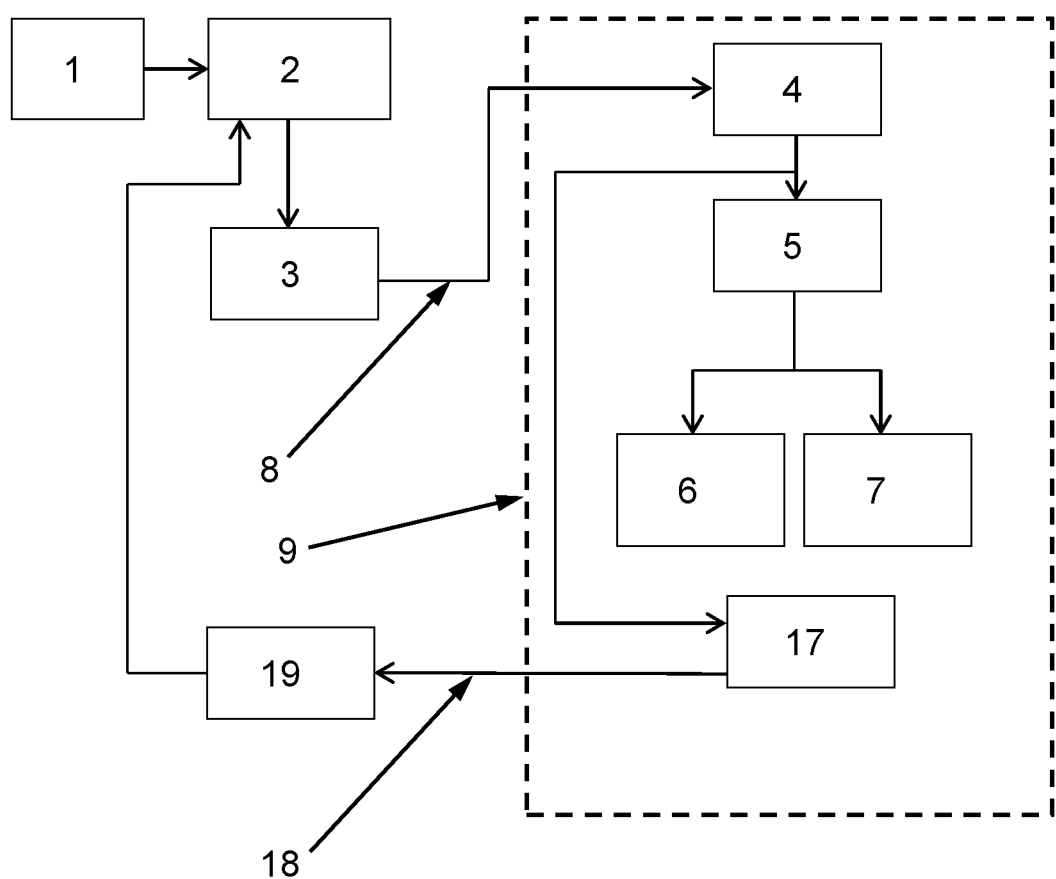
FIG. 3 shows the diagram of the embodiment of the invention shown in FIG. 1, where a second electrical to optical converter, a second fiber optic cable, and a second optical to electrical converter have been added.

FIG. 3 shows the diagram of the embodiment of the invention shown in FIG. 1, where a second electrical to optical converter 17, a second fiber optic cable 18, and a second optical to electrical converter 19 have been added. The electrical signal from the optical to electrical converter 4 is also sent as an electrical verification signal to the electrical to optical converter 17, which transforms the electrical verification signal to an optical verification signal sent through the second fiber optic cable 18 out of the MRI room 9 to the second optical to electrical converter 19, which transforms the optical verification signal back to the electrical verification signal, which is then compared to the predefined electrical signal generated by the signal generator 2.

FURTHER DETAILS OF THE PRESENT DISCLOSURE

The present disclosure may be described by the following items:
1. A system for generating a predefined electrical signal in an MR scanner for use in electrical stimulation of a subject during MRI or functional MRI of said subject, said MR scanner located inside a shielded MRI room, the system comprising:
   a control unit to be located outside the MRI room for generating an electrical signal,
   an electrical to optical converter to be located outside the MRI room for converting said electrical signal to a corresponding optical signal,
   an optical transmitting element, such as an optical fiber, for transmitting the optical signal into the MRI room, and
   an optical to electrical converter for converting the optical signal to said predefined electrical signal for electrical stimulation of the subject during magnetic resonance imaging, said optical to electrical converter configured for 1) being located inside the MRI room, and 2) operation during magnetic resonance imaging.
2. The system according to item 1, wherein the electrical stimulation of the subject is selected from the group of: deep brain stimulation, spinal cord stimulation, transcutaneous nerve stimulation, peripheral nerve stimulation, cranial nerve stimulation, vagus nerve stimulation, electrical muscle stimulation, cortical multi-electrode stimulation, retinal multi-electrode stimulation, gastric electrical stimulation therapy, cardiac stimulation, surface electrical stimulation, non-invasive electrical stimulation, transcorneal electrical stimulation (TES), whole-eye electrical stimulation (WES), transcutaneous electrical nerve stimulation (TENS), subcutaneous nerve stimulation, neuromuscular electrical stimulation (NMES), bionic replacements/bionic implants/neuroprosthetics, cochlear implants, and electroceuticals/electrobionics.
3. The system according to any of the preceding items, wherein the electrical to optical converter uses a transistor for converting the signal.

4. The system according to any of the preceding items, wherein the optical to electrical converter is a solar cell, preferably a photodiode.
5. The system according to any of the preceding items, wherein the optical to electrical converter uses an optocoupler for converting the signal.
6. The system according to any of the preceding items, wherein the fiber optic cable comprises at least one single-mode fiber for transmitting the optical signal.
7. The system according to any of the preceding items, wherein the optical to electrical converter is powered by a battery.
8. The system according to any of the preceding items, wherein the parameters defining the electrical signal for the electrical stimulation of the subject include one or more of the stimulation voltage, stimulation current, impedance of the system, stimulation frequency, stimulation duty cycle, total duration of the stimulation signal and the waveform of the stimulation signal.
9. The system according to any of the preceding items, wherein at least part of the electrical signal for the electrical stimulation of the subject is periodic with a rectangular waveform, or a square waveform, or a triangle waveform, or a sinusoidal waveform, or a cosine waveform, or a sawtooth waveform, or a ramp waveform, or an exponential waveform.
10. The system according to item 9, wherein the electrical signal changes between two or more of the waveforms listed in item 9.
11. The system according to any of the preceding items, wherein the electrical signal for the electrical stimulation of the subject is pulsating or alternating or switching between pulsating and alternating.
12. The system according to any of the preceding items, wherein the voltage of the electrical stimulation signal is in the range 0.1-10 V, or in the range 0.5-8.0 V, or in the range 1.0-6.0 V, or in the range 1.5-5.0 V, or in the range 2.0-4.0 V, or in the range 2.5-3.5 V.
13. The system according to any of the preceding items, wherein the frequency of the electrical stimulation signal is in the range 20-240 Hz, or in the range 60-200 Hz, or in the range 80-180 Hz, or in the range 100-160 Hz, or in the range 120-140 Hz.
14. The system according to any of the preceding items, wherein the electrical stimulation signal is comprised of multiple frequencies.
15. The system according to any of the preceding items, wherein the duty cycle of the electrical stimulation signal is less than 0.4, or less than 0.25, or less than 0.15, or less than 0.1, or less than 0.05, or less than 0.03.
16. The system according to any of the preceding items, wherein the pulse width is in the range 10-500 microseconds, or in the range 30-350 microseconds, or in the range 50-250 microseconds, or in the range 70-180 microseconds, or in the range 80-120 microseconds.
17. The system according to any of the preceding items, wherein the impedance of the system is in the range 1100-1400 Ohm, or in the range 800-1700 Ohm, or in the range 600-1900 Ohm, or in the range 300-2200 Ohm.
18. The system according to any of the preceding items, wherein at least one of the stimulation voltage, stimulation current, impedance of the system, stimulation frequency and stimulation duty cycle is varied during the electrical stimulation of the subject.
19. The system according to any of the preceding items, configured for, during magnetic resonance imaging: 1) monitoring the electrical stimulation signal delivered to the subject to generate an electrical verification signal, 2) converting said electrical verification signal to an optical verification signal, 3) transmitting said optical verification signal out of the MRI room, and 4) converting said optical verification signal to an electrical signal for monitoring the stimulation delivered to the subject in real time.
20. The system according to item 19, wherein said optical verification signal is transmitted out of the MRI room using a separate fiber optic cable or using the fiber optic cable used for transmitting the optical stimulation signal into the MRI room.
21. The system according to any of the preceding items, further comprising a computer configured for receiving input parameters for the electrical stimulation and configured for controlling the equipment.
22. The system according to any of the preceding items, further comprising an oscilloscope configured for generating the electrical stimulation signal.
23. The system according to item 22, wherein the oscilloscope is configured for receiving a signal from the computer, said signal defining the electrical stimulation signal.
24. A system for electrical stimulation of a subject during MRI or functional MRI of said subject, the system comprising:
the system for generating a predefined electrical signal according to any of items 1 to 23, and
at least one electrode configured for being implanted in the subject and configured for delivering the electrical stimulation to the subject based on said predefined electrical signal.
25. The system according to item 24, wherein the at least one electrode contains a plurality of contacts for delivering the electrical stimulation to the subject.
26. A method for generating a predefined electrical stimulation signal for electrical stimulation of a subject during MRI or functional MRI wherein said subject is located in an MR scanner located inside a shielded MRI room, the method comprising the steps of:
generating an electrical signal outside the MRI room,
converting the electrical signal to an optical signal outside the MRI room,
transmitting the optical signal into the MRI room, and
converting the optical signal to said predefined electrical stimulation signal inside the MRI room.
27. The method according to item 26, wherein the predefined electrical stimulation signal is suitable for: deep brain stimulation, spinal cord stimulation, transcutaneous nerve stimulation, peripheral nerve stimulation, cranial nerve stimulation, vagus nerve stimulation, electrical muscle stimulation, cortical multi-electrode stimulation, retinal multi-electrode stimulation, gastric electrical stimulation therapy, cardiac stimulation, surface electrical stimulation, non-invasive electrical stimulation, transcorneal electrical stimulation (TES), whole-eye electrical stimulation (WES), transcutaneous electrical nerve stimulation (TENS), subcutaneous nerve stimulation, neuromuscular electrical stimulation (NMES), bionic replacements/bionic implants/neuro-prosthetics, cochlear implants, or electroceuticals/electrobionics.
28. The method according to any of items 26 to 27, further comprising the steps of:

generating an electrical verification signal inside the MRI room from the predefined electrical stimulation signal, converting said electrical verification signal to an optical verification signal, transmitting said optical verification signal out of the MRI room, and converting said optical verification signal to an electrical signal for monitoring the stimulation delivered to the subject in real time.

29. A method for electrical stimulation of a subject during MRI or functional MRI of said subject in an MR scanner located inside a shielded MRI room, the method comprising the steps of:

converting an electrical stimulation signal to an optical signal outside the MRI room, transmitting the optical signal inside the MRI room using a fiber optic cable, converting the optical signal back to the electrical stimulation signal inside the MRI room, and subjecting the subject to the electrical stimulation signal.

30. The method according to item 29, wherein the type of treatment for which the method is used is selected from the group of: deep brain stimulation, spinal cord stimulation, transcutaneous nerve stimulation, peripheral nerve stimulation, cranial nerve stimulation, vagus nerve stimulation, electrical muscle stimulation, cortical multi-electrode stimulation, retinal multi-electrode stimulation, gastric electrical stimulation therapy, cardiac stimulation, surface electrical stimulation, non-invasive electrical stimulation, transcorneal electrical stimulation (TES), whole-eye electrical stimulation (WES), transcutaneous electrical nerve stimulation (TENS), subcutaneous nerve stimulation, neuromuscular electrical stimulation (NMES), bionic replacements/bionic implants/neuroprosthetics, cochlear implants, and electroceuticals/electrobionics.

31. The method according to any of items 29 to 30, further comprising the step of converting the electrical stimulation signal delivered to the patient inside the MRI room to an optical signal and transmitting said optical signal outside the MRI room through a fiber optic cable.

32. The method according to any of items 29 to 31, further comprising the step of inputting stimulation parameters to a computer configured for generating commands for the electrical stimulation.

The invention claimed is:

1. A system including an MR scanner for generating a predefined electrical signal in said MR scanner for use in electrical stimulation of a subject during functional MM of said subject performed in said MR scanner, said MR scanner located inside a shielded MRI room, the system comprising:

a control unit to be located outside the MRI room for generating an electrical signal, an electrical to optical converter to be located outside the MM room for converting said electrical signal to a corresponding optical signal, an optical transmitting element for transmitting the optical signal into the MM room, and an optical to electrical converter for converting the optical signal to said predefined electrical signal for electrical stimulation of the subject during magnetic resonance imaging, said optical to electrical converter configured for 1) being located inside the MRI room, and 2) operation during magnetic resonance imaging.

2. The system according to claim 1, wherein the electrical stimulation of the subject is selected from the group of: deep brain stimulation, spinal cord stimulation, transcutaneous nerve stimulation, peripheral nerve stimulation, cranial nerve stimulation, vagus nerve stimulation, electrical muscle stimulation, cortical multi-electrode stimulation, retinal multi-electrode stimulation, gastric electrical stimulation therapy, cardiac stimulation, surface electrical stimulation, non-invasive electrical stimulation, transcorneal electrical stimulation (TES), whole-eye electrical stimulation (WES), transcutaneous electrical nerve stimulation (TENS), subcutaneous nerve stimulation, neuromuscular electrical stimulation (LAMES), bionic replacements/bionic implants/neuroprosthetics, cochlear implants, and electroceuticals/electrobionics.

3. The system according to claim 1, wherein the optical to electrical converter is a solar cell or a photodiode.

4. The system according to claim 1, wherein the optical to electrical converter is powered by a battery.

5. The system according to claim 1, further comprising means for controlling parameters defining the electrical signal for the electrical stimulation of the subject, and wherein the parameters include one or more of the stimulation voltage, stimulation current, impedance of the system, stimulation frequency, stimulation duty cycle, total duration of the stimulation signal and the waveform of the stimulation signal.

6. The system according to claim 1, wherein the voltage of the electrical stimulation signal is in the range 0.1-10 V, or in the range 0.5-8.0 V, or in the range 1.0-6.0 V, or in the range 1.5-5.0 V, or in the range 2.0-4.0 V, or in the range 2.5-3.5 V.

7. The system according to claim 1, wherein the frequency of the electrical stimulation signal is in the range 20-240 Hz, or in the range 60-200 Hz, or in the range 80-180 Hz, or in the range 100-160 Hz, or in the range 120-140 Hz.

8. The system according to claim 1, wherein the pulse width is in the range 10-500 microseconds, or in the range 30-350 microseconds, or in the range 50-250 microseconds, or in the range 70-180 microseconds, or in the range 80-120 microseconds.

9. The system according to claim 1, wherein the impedance of the system is in the range 1100-1400 Ohm, or in the range 800-1700 Ohm, or in the range 600-1900 Ohm, or in the range 300-2200 Ohm.

10. The system according to claim 1, wherein at least one of the stimulation voltage, stimulation current, impedance of the system, stimulation frequency and stimulation duty cycle is varied during the electrical stimulation of the subject.

11. The system according to claim 1, configured for, during magnetic resonance imaging: monitoring the electrical stimulation signal delivered to the subject, the system comprising the optical to electrical converter for generating an electrical verification signal from the predefined electrical stimulation signal, a second electrical to optical converter for converting said electrical verification signal to an optical verification signal, a second optical transmitting element or the optical transmitting element for transmitting said optical verification signal out of the MM room, and a second optical to electrical converter for converting said optical verification signal to an electrical signal for monitoring the stimulation delivered to the subject in real time.

12. A system for electrical stimulation of a subject during functional Mill of said subject, the system comprising:
   the system for generating a predefined electrical signal according to claim 1, and
   at least one electrode configured for being implanted in the subject and configured for delivering the electrical stimulation to the subject based on said predefined electrical signal.

13. The system according to claim 12, wherein the at least one electrode contains a plurality of contacts for delivering the electrical stimulation to the subject.

14. A method for generating a predefined electrical stimulation signal for electrical stimulation of a subject during functional Mill wherein said subject is located in an MR scanner located inside a shielded MM room, the method comprising:
   generating an electrical signal outside the MM room,
   converting the electrical signal to an optical signal outside the Mill room,
   transmitting the optical signal into the MM room, and
   converting the optical signal to said predefined electrical stimulation signal inside the MRI room for electrical stimulation of the subject during magnetic resonance imaging.

15. The method according to claim 14, wherein the predefined electrical stimulation signal is suitable for: deep brain stimulation, spinal cord stimulation, transcutaneous nerve stimulation, peripheral nerve stimulation, cranial nerve stimulation, vagus nerve stimulation, electrical muscle stimulation, cortical multi-electrode stimulation, retinal multi-electrode stimulation, gastric electrical stimulation therapy, cardiac stimulation, surface electrical stimulation, non-invasive electrical stimulation, transcorneal electrical stimulation (TES), whole-eye electrical stimulation (WES), transcutaneous electrical nerve stimulation (TENS), subcutaneous nerve stimulation, neuromuscular electrical stimulation (LAMES), bionic replacements/bionic implants/neuroprosthetics, cochlear implants, or electroceuticals/electrobionics.

16. The method according to claim 14, further comprising:
   generating an electrical verification signal inside the MM room from the predefined electrical stimulation signal,
   converting said electrical verification signal to an optical verification signal,
   transmitting said optical verification signal out of the MM room, and
   converting said optical verification signal to an electrical signal for monitoring the stimulation delivered to the subject in real time.

* * * * *

UNITED STATES PATENT AND TRADEMARK OFFICE
CERTIFICATE OF CORRECTION

PATENT NO. : 11,554,261 B2
APPLICATION NO. : 16/650713
DATED : January 17, 2023
INVENTOR(S) : Anders Ohlhues Baandrup, Louise Møller Jørgensen and Carsten Thomsen It is certified that error appears in the above-identified patent and that said Letters Patent is hereby corrected as shown below:

In the Claims

In Claim 1, Column 13, Line 52, delete "MM" and insert -- MRI --.

In Claim 1, Column 13, Line 58, delete "MM" and insert -- MRI --.

In Claim 1, Column 13, Line 61, delete "MM" and insert -- MRI --.

In Claim 2, Column 14, Line 13, delete "(LAMES)," and insert -- (NMES), --.

In Claim 11, Column 14, Line 63, delete "MM" and insert -- MRI --.

In Claim 12, Column 15, Line 2, delete "Mill" and insert -- MRI --.

In Claim 14, Column 15, Line 14, delete "Mill" and insert -- MRI --.

In Claim 14, Column 15, Line 15, delete "MM" and insert -- MRI --.

In Claim 14, Column 15, Line 17, delete "MM" and insert -- MRI --.

In Claim 14, Column 15, Line 19, delete "Mill" and insert -- MRI --.

In Claim 14, Column 15, Line 20, delete "MM" and insert -- MRI --.

In Claim 15, Column 16, Line 11, delete "(LAMES)," and insert -- (NMES), --.

In Claim 16, Column 16, Line 16, delete "MM" and insert -- MRI --.

In Claim 16, Column 16, Line 20, delete "MM" and insert -- MRI --.

Signed and Sealed this
Twenty-eighth Day of March, 2023

Katherine Kelly Vidal
*Director of the United States Patent and Trademark Office*